United States Patent [19]

Müller et al.

[11] Patent Number: 5,188,622
[45] Date of Patent: Feb. 23, 1993

[54] VACUUM BOTTLE FOR COLLECTION OF BODY FLUIDS

[75] Inventors: Walter Müller, Kestenholz; Silvan Nützi, Wolfwil; Alessandro Born, Oensingen, all of Switzerland

[73] Assignee: Genossenschaft Vebo, Solothurnische Eingliederungsstatte fur Behinderte, Oensingen, Switzerland

[21] Appl. No.: 749,138

[22] Filed: Aug. 23, 1991

[30] Foreign Application Priority Data

Aug. 29, 1990 [CH] Switzerland .................. 2811/90

[51] Int. Cl.$^5$ .............................................. A61M 1/00
[52] U.S. Cl. ..................................... 604/319; 215/321
[58] Field of Search .............. 108/760; 604/317, 319, 604/403; 215/316–318, 321, 341

[56] References Cited

U.S. PATENT DOCUMENTS

| | | | |
|---|---|---|---|
| 686,642 | 11/1901 | Wayte | 215/316 |
| 895,066 | 8/1908 | Brewington | 215/316 |
| 3,276,642 | 10/1966 | Johnson et al. | 215/321 |
| 3,782,414 | 1/1974 | Holbrook | 604/319 |
| 3,907,146 | 9/1975 | Fields | 215/321 |
| 4,376,439 | 3/1983 | Lauterjung | 604/319 |
| 4,397,643 | 8/1983 | Rygiel | 604/317 |
| 4,455,140 | 6/1984 | Joslin | 604/317 |

FOREIGN PATENT DOCUMENTS 2334580  7/1977  France .

*Primary Examiner*—Max Hindenburg
*Attorney, Agent, or Firm*—Peter K. Kontler

[57] ABSTRACT

A vacuum bottle for collection of pus has a vessel of pressure- and temperature-resistant plastic material. The outlet of the neck of the vessel is surrounded by a collar which has a plane end face and extends radially outwardly beyond the external surface of the neck, the same as an annular rib which is spaced apart from the collar. The end face is adjacent a membrane-like end wall of a cupped elastic cover having a cylindrical skirt which surrounds the neck and has an internal shoulder engaging an external shoulder of the rib to separably couple the cover to the bottle. The end wall is connected with one end of a conduit the other end of which can draw pus from a wound. The pressure in the vessel is reduced below atmospheric pressure by heating the vessel so that the air therein expands and escapes between the neck and the skirt of the cover. The vessel is thereupon cooled whereby the end wall penetrates into the outlet and sealingly engages the end face of the collar.

15 Claims, 1 Drawing Sheet

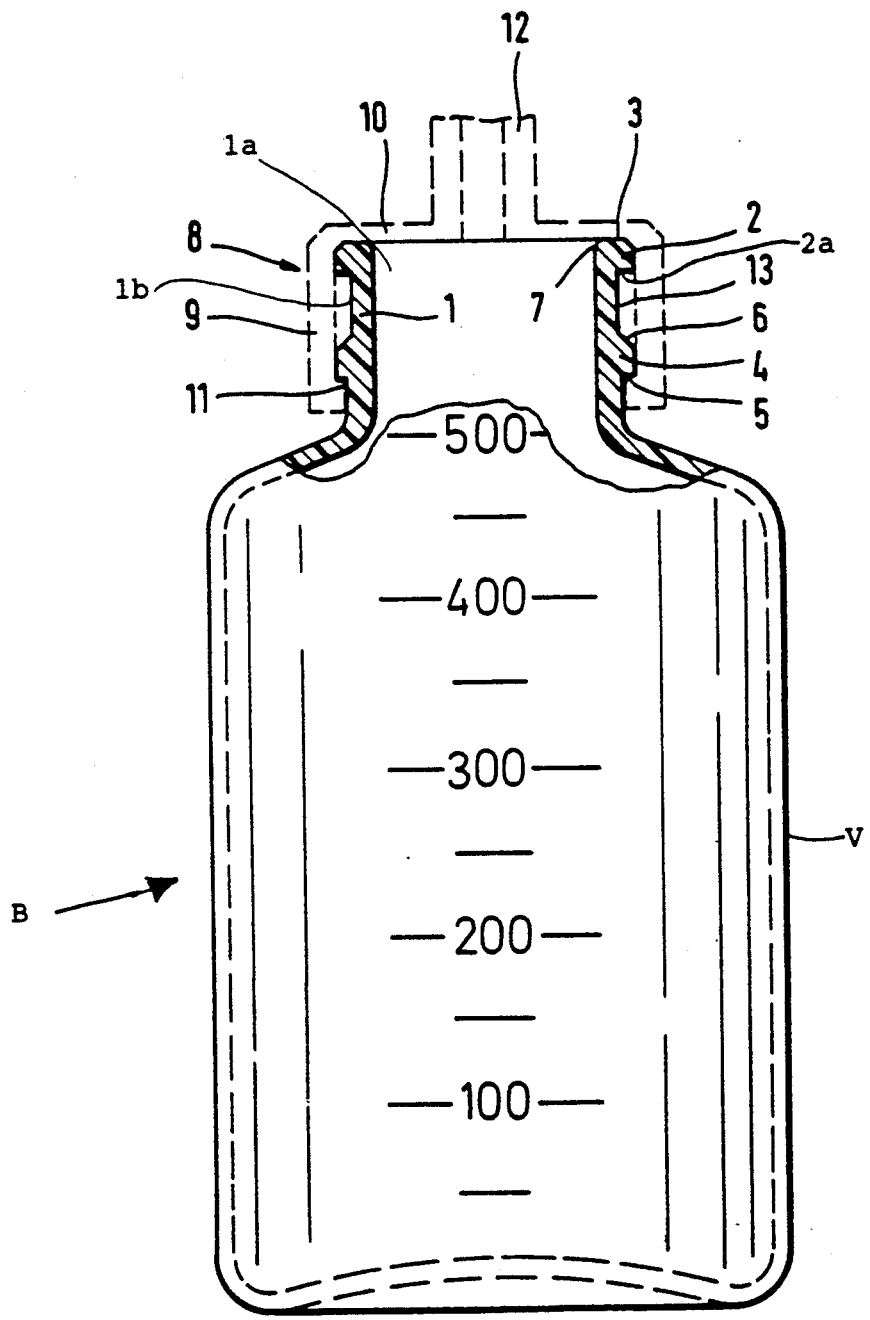

VACUUM BOTTLE FOR COLLECTION OF BODY FLUIDS

BACKGROUND OF THE INVENTION

The invention relates to vacuum bottles in general, and more particularly to improvements in bottles of the type disclosed in commonly owned U.S. Pat. Nos. 4,161,257 and 4,220,251 to Hauri and in published European patent application No. 0 288 679. Such bottles can be used for evacuation of pus or other body fluids from wounds or other body cavities while their internal spaces are maintained below atmospheric pressure.

The European patent application discloses a bottle having a neck with a cylindrical external surface and defining an outlet surrounded by a plane end face which, in turn, is surrounded by an undercut shoulder. A closure of elastomeric material has an end wall adjacent the end face of the neck and a cylindrical portion which surrounds the neck and has an internal shoulder engaging the undercut shoulder of the neck. The end wall of the closure is flat and is connected with one end of a conduit which can receive pus from a wound. In order to facilitate evacuation of air from the bottle, the internal surface of the cylindrical portion of the closure is configured in such a way that it defines a passage for the escape of air from the bottle. The bottle is made of glass which creates the danger of implosion when the pressure within the bottle is below atmospheric pressure. Moreover, the making of a specially designed closure (which defines the aforementioned air evacuating passage or passages) contributes to the initial cost of the bottle-closure combination. Still further, the neck of the bottle must have a large outer diameter in the region of the outlet in order to establish an external shoulder which can be reliably engaged by the cylindrical portion of the closure.

OBJECTS OF THE INVENTION

An object of the invention is to provide a vacuum bottle which is safer than heretofore known bottles.

Another object of the invention is to provide a bottle which can be used with a simple, inexpensive and versatile cover or closure.

A further object of the invention is to provide a bottle-closure combination which is less likely to implode than a conventional bottle.

An additional object of the invention is to provide the bottle with a novel and improved neck.

Still another object of the invention is to simplify the reduction of pressure in the bottle preparatory to use of the bottle for the evacuation of body fluids.

SUMMARY OF THE INVENTION

One feature of the present invention resides in the provision of a vacuum bottle for collection of body fluids which are discharged by wounds or other body cavities. The improved bottle comprises a vessel which is preferably made of a transparent or translucent material and includes a neck which defines an outlet. The neck has an external surface and includes a collar which surrounds the outlet and has a plane end face engageable by a substantially cupped cover which is to seal the outlet during collection of a body fluid in the vessel. The collar extends outwardly beyond the external surface of the neck, and the latter further comprises at least one substantially annular projection which extends beyond the external surface and is spaced apart from the collar. The at least one projection has a shoulder which faces away from the collar and is engageable by an internal shoulder of the cover. The neck and/or the vessel consists of a pressure- and temperature-resistant (i.e., heatable and preferably unbreakable) material, preferably a plastic material.

The collar has a first outer diameter, the external surface of the neck has a second outer diameter which is smaller than the first outer diameter, and the at least one projection has a third outer diameter which preferably matches or at least approximates the first outer diameter.

The collar is preferably provided with a first facet which confronts the at least one projection, and the at least one projection has a second facet which confronts the first facet and is inclined relative thereto. At least one of the facets can constitute or resemble a conical frustum.

The collar can further include a convex annular surface which is surrounded by and merges into the end face and also extends into the outlet of the neck.

The at least one projection may but need not constitute a circumferentially complete rib.

Another feature of the invention resides in the provision of a combination which includes a substantially cup-shaped elastic cover and a bottle. The cover includes a preferably membrane-like end wall and a tubular skirt which extends from one side of the end wall and has an internal shoulder remote from the end wall. The bottle comprises a vessel having a neck which defines an outlet adjacent the one side of the end wall. The external surface of the neck is surrounded by the skirt of the cover, and the neck further comprises a collar which surrounds the outlet and has a plane end face at the one side of the end wall of the cover. Still further, the neck has a substantially annular projection which extends outwardly beyond the external surface and has a shoulder facing away from the collar and being engaged by the internal shoulder of the skirt. The collar extends outwardly beyond the external surface of the neck, and the neck and/or the vessel consists of a pressure- and temperature-resistant material.

The collar can be provided with a convex annular surface which is surrounded by and merges into the plane end face and extends into the outlet of the neck.

The collar and the projection can be provided with confronting facets which are inclined relative to each other.

The end wall is sufficiently pliable to penetrate into the outlet when the pressure in the bottle is reduced by first heating the vessel (to thereby effect expansion of air and/or vapors in the bottle and expulsion of some air and/or vapors between the skirt and the external surface of the neck) and by thereupon cooling the vessel so that the pressure of atmospheric air at the exterior of the end wall suffices to press the end wall into the outlet whereby the end wall overlies the plane end face as well as the convex annular surface of the collar.

The novel features which are considered as characteristic of the invention are set forth in particular in the appended claims. The improved bottle-closure combination itself, however, both as to its construction and the mode of using the same, together with additional features and advantages thereof, will be best understood upon perusal of the following detailed description of certain presently preferred specific embodiments with reference to the accompanying drawing.

BRIEF DESCRIPTION OF THE DRAWING

The single FIGURE of the drawing is a partly elevational and partly central sectional view of a vacuum bottle which embodies one form of the invention, a cup-shaped closure or cover for the outlet in the neck of the bottle being indicated by broken lines.

DESCRIPTION OF PREFERRED EMBODIMENTS

The improved bottle-cover combination comprises a bottle B including a vessel V and a neck 1 with an outlet 1a. The vessel V can constitute an elongated cylinder, the same as the neck 1. The entire bottle B is made of a preferably transparent or translucent plastic material which is resistant to heat and to deforming stresses including pressure (i.e., it is not brittle). The outlet 1a of the neck 1 is surrounded by a ring-shaped collar 2 having a preferably plane end face 3 and an annular convex surface 7 which is surrounded by and merges gradually into the end face 3 and extends into the outlet 1a. The collar 2 extends radially outwardly beyond the preferably cylindrical external surface 1b of the neck 1, the same as an annular projection 4 (e.g., a circumferentially complete rib) which is spaced apart from the collar 2 and has an annular shoulder 5 facing away from the collar 2. A frustoconical facet 6 of the projection 4 confronts a plane or frustoconical facet 2a of the collar 2. The customary graduations of the vessel V are intended to denote (e.g., in cubic centimeters) the quantity of body liquid which accumulates in the bottle B.

The cover or closure 8 of the improved combination is made of an elastomeric material and includes a membrane-like end wall 10 as well as a tubular (preferably cylindrical) skirt 9 which extends from one side of the end wall 10 and surrounds the neck 1 of the bottle B. That end of the skirt 9 which is remote from the end wall 10 has an internal shoulder 11 which engages the shoulder 5 of the projection 4 when the cover 8 is properly applied over the neck 1. The central portion of the end wall 10 is connected with one end of a flexible conduit 12 the other end of which can be positioned to gather pus or another body fluid.

The outer diameter of the collar 2 preferably matches or approximates the outer diameter of the projection 4, and each of these parts extends radially outwardly beyond the external surface 1b of the neck 1. This ensures that the external surface 1b and the internal surface of the skirt 9 define a ring-shaped compartment 13 which extends between the facets 2a and 6 when the cover 8 is properly applied over the neck 1.

The circumferentially complete rib-shaped projection 4 can be replaced with an interrupted projection, e.g., with a rib which consists of several arcuate sections and has axially parallel clearances or gaps between neighboring sections. Such clearances communicate with the compartment 13. The shoulder 5 is then a composite shoulder having several arcuate portions each defined by one arcuate section of an interrupted projection.

The cover 8 can be made of rubber or of a similar elastomeric material which can be expanded so that the shoulder 11 can be slipped over the collar 2 and thereupon over the projection 4 before it engages the shoulder 5. The inner side of the end wall 10 can sealingly engage the end face 3 as well as the convex annular surface 7, depending upon the extent of penetration of the end wall 10 into the outlet 1a in response to the establishment of a differential between the atmospheric pressure and the pressure in the bottle B.

In order to reduce the pressure in the bottle B, the non-illustrated end of the conduit 12 is sealed by a clamp, by a plug or in any other suitable way while the end wall 10 of the cover 8 sealingly engages the end face 3 of the collar 2 and the internal shoulder 11 of the skirt 9 engages the shoulder 5 of the projection 4. The bottle B is then heated in any suitable way, e.g., by a flame or by contact with a heated fluid, so that the air and/or vapors which are entrapped in the vessel V expand and cause the membrane-like end wall 10 to bulge outwardly whereby the inner side of the end wall 10 is lifted off the plane end face 3 and air and/or vapors are free to escape along the end face 3, around the collar 2 and into the compartment 13 whence they escape into the atmosphere around the one-piece projection 4 or around and between the sections of a composite projection. The sealing action between the projection 4 and the shoulder 11 is preferably negligible or nil (at least while the end wall 10 bulges outwardly) so that heated air and/or vapors which have been expelled from the vessel V into the compartment 13 are free to escape into the atmosphere.

The bottle B is then sterilized and cooled whereby the pressure in the vessel V drops below atmospheric pressure. Consequently, the pressure of atmospheric air against the outer side of the membrane-like end wall 10 suffices to flex this wall inwardly into pronounced sealing engagement with the plane end face 3 as well as with the convex surface 7 of the collar 2, i.e., the compartment 13 is reliably sealed from the outlet 1a and hence from the interior of the neck 1 and vessel V. The sealing action between the collar 2 and the end wall 10 is highly reliable because the area of sealing contact is rather large, i.e., the inner side of the end wall 10 engages the plane end face 3 as well as the convex surface 7 of the collar.

The purpose of the facets 2a, 6 is to facilitate the application of the skirt 9 onto and its separation from the neck 1.

An important advantage of the improved bottle B is that the likelihood of implosion is greatly reduced because the material of the neck 1 and/or vessel V is not brittle. This is highly desirable and advantageous, for example, when the improved bottle-cover combination is used in an operating room. The preferably plastic material of the bottle B can be readily selected in such a way that it can stand pronounced compressive and expanding stresses, e.g., in the course of a sterilizing operation, that it can be repeatedly heated to elevated temperatures, that the overall weight of the bottle is low, and that the accumulation of a fluid in the vessel V can be observed at all times.

Another important advantage of the improved bottle-cover combination is that the sealing action between the cover and the neck 1 of the bottle B improves as the pressure in the interior of the bottle decreases.

The presently preferred material of the bottle is polysulfone.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A vacuum bottle for collection of body fluids, comprising a vessel having a neck with an outlet, said neck having an external surface and including a collar surrounding said outlet and having a plane end face engageable by a substantially cupped cover which is to seal said outlet during collection of a body fluid in said vessel, said collar extending outwardly beyond said external surface, and said neck further comprising at least one substantially annular projection extending beyond said external surface, said at least one projection having a shoulder which faces away from said collar and is engageable by an internal shoulder of the cover, and at least said vessel consisting of a pressure- and temperature-resistant material to withstand suction and thermal sterilization without significant deformation.

2. The bottle of claim 1, wherein said material is a plastic material.

3. The bottle of claim 1, wherein said collar has a first outer diameter, said external surface has a second outer diameter smaller than said first diameter, and said at least one projection has a third outer diameter which equals or approximates said first diameter.

4. The bottle of claim 1, wherein said collar has a first facet which confronts said at least one projection and said at least one projection has a second facet which confronts said collar, said facets being inclined relative to each other.

5. The bottle of claim 1, wherein said collar has a convex annular surface which is surrounded by said end face and merges into said end face and extends into said outlet.

6. The bottle of claim 1, wherein said at least one projection is a circumferentially complete rib.

7. The bottle of claim 1, wherein said at least one projection is spaced from said collar.

8. The combination of a substantially cup-shaped elastic cover having a membrane-like end wall and a tubular skirt extending from one side of said end wall and having an annular internal shoulder remote from said end wall, with a vacuum bottle for collection of body fluids, said bottle comprising a vessel having a neck which defines an outlet adjacent said one side of said end wall, and said neck having an external surface which is surrounded by said skirt, a collar surrounding said outlet and having a plane end face at said one side of said end wall, and at least one substantially annular projection extending outwardly beyond said external surface and having a shoulder facing away from said collar and engaged by said internal shoulder, said collar extending outwardly beyond said external surface, and at least said vessel consisting of a pressure- and temperature-resistant material to withstand suction and thermal sterilization without significant deformation.

9. The structure of claim 8, wherein said collar has a convex annular surface surrounded by and merging into said end face and extending into said outlet.

10. The structure of claim 8, wherein said collar and said projection have confronting facets which are inclined relative to each other.

11. The bottle of claim 10, wherein said at least one projection is spaced from said collar.

12. A vacuum bottle for collection of body fluids, comprising a vessel having a neck with an outlet, said neck having an external surface and including a collar surrounding said outlet and having a plane end face engageable by a substantially cupped cover which is to seal said outlet during collection of a body fluid in said vessel, said collar extending outwardly beyond said external surface, and said neck further comprising at least one substantially annular projection extending beyond said external surface, said collar having a first outer diameter, said external surface having a second outer diameter smaller than said first diameter, and said at least one projection having a third outer diameter which equals or approximates said first diameter, said at least one projection having a shoulder which faces away from said collar, is substantially parallel to said end face and is engageable by an internal shoulder of the cover, and at least said vessel consisting of a pressure- and temperature-resistant plastic material to withstand suction and thermal sterilization without significant deformation.

13. The bottle of claim 12, wherein said at least one projection is spaced from said collar.

14. The combination of a substantially cup-shaped elastic cover having a membrane-like end wall and a tubular skirt extending from one side of said end wall and having an annular internal shoulder remote from said end wall, with a vacuum bottle for collection of body fluids, said bottle comprising a vessel having a neck which defines an outlet adjacent said one side of said end wall, and said neck having an external surface which is surrounded by said skirt, a collar surrounding said outlet and having a plane end face at said one side of said end wall, and at least one substantially annular projection extending outwardly beyond said external surface and having a shoulder facing away from said collar and engaged by said internal shoulder, said shoulder of said projection being substantially parallel to said end face, and said collar extending outwardly beyond said external surface and having a first outer diameter, said external surface having a second outer diameter smaller than said first diameter, and said at least one projection having a third outer diameter which equals or approximates said first diameter, at least said vessel consisting of a pressure- and temperature-resistant plastic material to withstand suction and thermal sterilization without significant deformation.

15. The structure of claim 14, wherein said at least one projection is spaced from said collar.

* * * * *